United States Patent
Choi et al.

(10) Patent No.: US 12,161,550 B2
(45) Date of Patent: *Dec. 10, 2024

(54) MULTIFOCAL LENS HAVING REDUCED VISUAL DISTURBANCES

(71) Applicant: Alcon Inc., Fribourg (CH)

(72) Inventors: Myoung-Taek Choi, Arlington, TX (US); Xin Hong, Fort Worth, TX (US); Yueai Liu, Arlington, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/479,314

(22) Filed: Oct. 2, 2023

(65) Prior Publication Data
US 2024/0024094 A1 Jan. 25, 2024

Related U.S. Application Data

(63) Continuation of application No. 17/664,531, filed on May 23, 2022, now Pat. No. 11,813,160, which is a continuation of application No. 16/864,254, filed on May 1, 2020, now Pat. No. 11,364,111, which is a continuation of application No. 15/051,765, filed on Feb. 24, 2016, now Pat. No. 10,675,146.

(51) Int. Cl.
*A61F 2/16* (2006.01)
*G02C 7/04* (2006.01)

(52) U.S. Cl.
CPC ............ *A61F 2/164* (2015.04); *A61F 2/1618* (2013.01); *A61F 2/1637* (2013.01); *A61F 2/1654* (2013.01); *G02C 7/041* (2013.01); *G02C 7/042* (2013.01); *G02C 7/049* (2013.01); *A61F 2/1613* (2013.01); *A61F 2002/1683* (2013.01); *G02C 2202/20* (2013.01)

(58) Field of Classification Search
CPC .... G02C 2202/20; G02C 7/042; G02C 7/041; G02C 7/049; A61F 2/1654; A61F 2/1613; A61F 2/1637; A61F 2/1618; A61F 2/164; A61F 2002/1683; A61F 2002/1681
USPC ............ 351/159.44, 159.35, 159.26, 159.15, 351/159.11
See application file for complete search history.

(56) References Cited

U.S. PATENT DOCUMENTS

2011/0270390 A1* 11/2011 Kobayashi ............ A61F 2/1618
623/6.38

FOREIGN PATENT DOCUMENTS

AU 2015201867 A1 * 4/2015 ............... A61F 2/14

* cited by examiner

*Primary Examiner* — Travis S Fissel
(74) *Attorney, Agent, or Firm* — Patterson + Sheridan, LLP

(57) ABSTRACT

A method and system provide an ophthalmic device. The ophthalmic device includes an ophthalmic lens having an anterior surface, a posterior surface, at least one diffractive structure and at least one base curvature. The at least one diffractive structure for provides a first spherical aberration for a first focus corresponding to at least a first focal length. The at least one base curvature provides a second spherical aberration for at least a second focus corresponding to at least a second focal length. The first spherical aberration and the second spherical aberration are provided such that the first focus has a first focus spherical aberration and the second focus has a second focus spherical aberration. The first focus spherical aberration is opposite in sign to the second focus spherical aberration.

16 Claims, 5 Drawing Sheets

MULTIFOCAL LENS HAVING REDUCED VISUAL DISTURBANCES

CROSS-REFERENCE TO RELATED APPLICATIONS

This application is a continuation of U.S. Non-Provisional patent application Ser. No. 17/664,531, filed May 23, 2022, which is a continuation of U.S. Non-Provisional patent application Ser. No. 16/864,254, filed on May 1, 2020, now issued as U.S. Pat. No. 11,364,111, which is a continuation of U.S. Non-Provisional patent application Ser. No. 15/051,765, filed on Feb. 24, 2016, now issued as U.S. Pat. No. 10,675,146, and are hereby incorporated by reference in their entirety as though fully and completely set forth herein.

BACKGROUND

Intraocular lenses (IOLs) are implanted in patients' eyes either to replace a patient's lens or, in the case of a phakic IOL, to complement the patient's lens. For example, the IOL may be implanted in place of the patient's lens during cataract surgery. Alternatively, a phakic IOL may be implanted in a patient's eye to augment the optical power of the patient's own lens.

Some conventional IOLs are single focal length IOLs, while others are multifocal IOLs. Single focal length IOLs have a single focal length or single power. Objects at the focal length from the eye/IOL are in focus, while objects nearer or further away may be out of focus. Although objects are in perfect focus only at the focal length, objects within the depth of field (within a particular distance of the focal length) still acceptably in focus for the patient to consider the objects in focus. Multifocal IOLs, on the other hand, have at least two focal lengths. For example, a bifocal IOL has two focal lengths for improving focus in two ranges: a far focus corresponding to a larger focal length and a near focus corresponding to a smaller focal length. Trifocal IOLs have three focuses: a far focus, a near focus and an intermediate focus corresponding to a focal length between that of the near and far focuses. Multifocal IOLs may improve the patient's ability to focus on distant and nearby objects. Such IOLs may be of particular use for patients suffering from presbyopia, which adversely affects the eye's ability to focus on both far and near objects.

Although multifocal lenses may be used to address conditions such as presbyopia, there are drawbacks. A patient may experience increased incidences of visual disturbances. Visual disturbances are unwanted side effects, such as ghost images, halos, glare or hazy vision, due to the multiple focuses of multifocal IOLs. For example, because of the different focal lengths, multiple images may be formed for a single object. One image due to the focal length in the appropriate distance range is in focus, while the ghost image due to the focal length of the other distance range is out of focus. Such ghost images are undesirable. As a result, the intensity and sharpness of ghost images are desired to be decreased. Similarly, it may be desirable to mitigate other visual disturbances for multi-focal lenses.

Accordingly, what is needed is a system and method for addressing visual disturbances in multifocal IOLs.

BRIEF SUMMARY OF THE INVENTION

A method and system provide an ophthalmic device. The ophthalmic device includes an ophthalmic lens having an anterior surface, a posterior surface, at least one diffractive structure and at least one base curvature. The at least one diffractive structure for provides a first spherical aberration for a first focus corresponding to at least a first focal length. The at least one base curvature provides a second spherical aberration for at least a second focus corresponding to at least a second focal length. The first spherical aberration and the second spherical aberration are provided such that the first focus has a first focus spherical aberration and the second focus has a second focus spherical aberration. The first focus spherical aberration is opposite in sign to the second focus spherical aberration.

DETAILED DESCRIPTION OF THE PREFERRED EMBODIMENTS

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. For example, the method and system are described primarily in terms of IOLs. However, the method and system may be used with contact lenses. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system provide an ophthalmic device. The ophthalmic device includes an ophthalmic lens having an anterior surface, a posterior surface, at least one diffractive structure and at least one base curvature. The at least one diffractive structure for provides a first spherical aberration for a first focus corresponding to at least a first focal length. The at least one base curvature provides a second spherical aberration for at least a second focus corresponding to at least a second focal length. The first spherical aberration and the second spherical aberration are provided such that the first focus has a first focus spherical aberration and the second focus has a second focus spherical aberration. The first focus spherical aberration is opposite in sign to the second focus spherical aberration.

Figure 1:
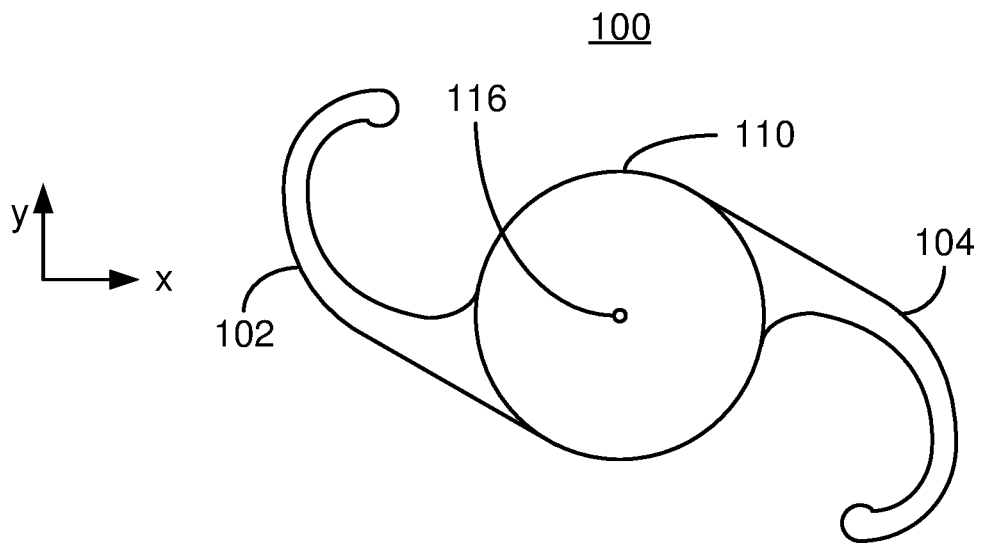
FIG. 1 depicts a plan view of an exemplary embodiment of an ophthalmic device.
Figure 2:
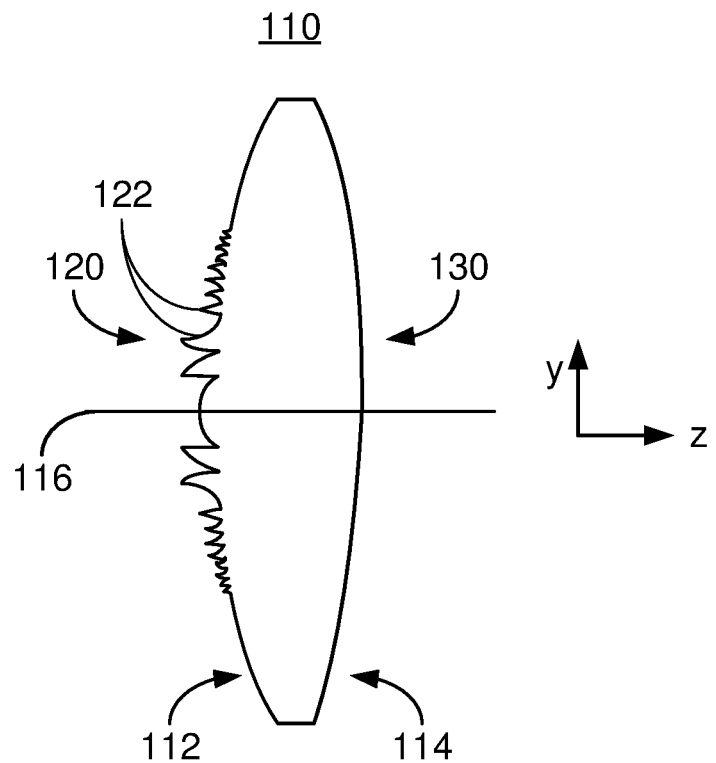
FIG. 2 depicts a side view of an exemplary embodiment of a lens of an ophthalmic device.

FIGS. 1-2 depict an exemplary embodiment of an ophthalmic device 100 that may be used as an IOL. FIG. 1 depicts a plan view of the ophthalmic device 100, while FIG. 2 depicts a side view of the ophthalmic lens 110. For clarity, FIGS. 1 and 2 are not to scale. The ophthalmic device 100 includes an ophthalmic lens 110 (herein after "lens") as well as haptics 102 and 104. The lens 110 may be made of a variety of optical materials including but not limited to one or more of silicone, a hydrogel, an acrylic and AcrySof®. Haptics 102 and 104 are used to hold the ophthalmic device 100 in place in a patient's eye (not explicitly shown). However, in other embodiments, other mechanism(s) might be used to retain the ophthalmic device in position in the eye. Thus, the haptics 102 and/or 104 might be omitted. For clarity, the haptics are not depicted in FIGS. 2-7, discussed below. Although the lens 110 is depicted as having a circular cross section in the plan view of FIG. 1, in other embodiments, other shapes may be used. Further, although described in the context of an IOL, the ophthalmic lens 110 may be a contact lens. In such a case, the haptics 102 would be omitted and the ophthalmic lens sized and otherwise configured to reside on the surface of the eye. Thus, the ophthalmic lens 110 may be an IOL or contact lens.

The lens 110 has an anterior surface 112 a posterior surface 114 and an optic axis 116. The lens is also characterized by a diffractive structure 120 and a base curvature 130. The lens 110 is a multifocal lens having multiple focal lengths. In order to provide multiple focuses, the anterior and/or posterior surface(s) of the lens 110 may have zones corresponding to different ranges in distance perpendicular to the optic axis 116 (i.e. different radii). Stated differently, a zone is an annular ring along the surface from a minimum radius to a maximum radius from the optic axis 116. For a zonal multifocal refractive lens, each zone may have a different focal length/power. To provide such a refractive lens, the base curvature 130 may be different in different zones. For a diffractive lens, light traveling through different zones of the diffractive structure 120 interferes. This zone-to-zone interference may result in multiple focal lengths for the lens. For example, the diffractive structure 120 may use different diffractive orders to create multiple focuses. For a bifocal diffractive structure 120, the $0^{th}$ diffraction order may be used for distance focus, and $+1^{st}$ diffraction order used for near focus. Alternatively, a $-1^{st}$ diffraction order may be used for distance focus, and $0^{th}$ diffraction order may be used for near focus. For a diffractive lens, the base curvature 130 is usually considered to have a single zone, or consistent shape, across the surface of the lens 110. In either the refractive or diffractive case, the lens 110 may be configured to have at least a first focal length corresponding to a near focus and a second focal length corresponding to a far focus. As their names imply, the near focus is closer to the ophthalmic lens 110 in a direction along the optic axis 116 than the far focus. The near focus thus has a shorter focal length than the far focus. The lens 110 may thus be a bifocal lens. The lens 110 may also have additional focal lengths. For example, the ophthalmic lens 110 may be a trifocal lens including the near focus and far focus described above as well as an intermediate focus between the near and far focuses. In other embodiments, the lens 110 may be configured to have another number of focal lengths and focuses.

The lens 110 includes the diffractive structure 120 on the anterior surface 112 of the lens 110 and a base curvature 130 on the posterior surface 114 of the lens 110. In other embodiments, the diffractive structure 120 and/or base curvature 130 may reside on different surfaces 112 and 114. The combination of the base curvature 130 and diffractive structure 130 introduce spherical aberrations that are opposite in sign into the far focus and near focus. A positive spherical aberration results in the lens refracting central rays (rays closer to the optic axis 116/center) that are parallel to the optic axis 116 less than if the lens was without the spherical aberration. Similarly, a positive spherical aberration results in the lens refracting marginal rays (rays further from the optic axis 116/closer to the edges) that are parallel to the optic axis 116 more than if the lens did not have the aberration. A negative spherical aberration results in the lens refracting central rays that are parallel to the optic axis 116 more than if the lens did not have the aberration. Similarly, a negative spherical aberration causes the lens to refract marginal rays that are parallel to the optic axis 116 less than if the lens were without the aberration.

The base curvature 130 may introduce a negative spherical aberration for at least one focus, while the diffractive structure 120 may introduce a positive spherical aberration for another focus. The magnitudes and signs of the spherical aberrations introduced by the base curvature 130 and the diffractive structure 120 may not be the same. The base curvature 130 may introduce negative spherical aberrations into both the near focus and far focus. The spherical aberrations introduced by the base curvature 130 usually have the same sign in for all focuses because the base curvature is generally a single zone for a diffractive multifocal lens. The positive spherical aberration may be introduced into the near focus by the diffractive structure 120. This may be accomplished by changing the period of step heights of the echelettes with increasing radial distance from the optic axis 116 from what the lowest order calculations would determine the period should be. It might also be possible to introduce a negative spherical aberration in one focus and a zero spherical aberration in another focus. Thus, the sign and/or magnitude of spherical aberrations introduced in different focuses by the diffractive structure 120 may be the same or different.

In some embodiments, other changes may be made to the portion of the lens 110 underlying the diffractive structure 120. Such changes will be described herein as changes to the base curvature 130. For example, the base surface may have multiple zones which have different powers and different spherical aberrations. In such embodiments, the multiple zone base curvature 130 may provide different spherical aberrations in different zones.

Mathematically, the base curvature 130 for a single zone base curve surface of the posterior surface 114 of the lens 110 may be described by:

$$z_{base} = [cr^2/(1+\operatorname{sqrt}(1-(1+k)c^2r^2))] + A_4 r^4 + A_6 r^6 + \quad (1)$$

where $z_{base}$ is the base curvature (the distance the lens surface extends in the z direction), r is the distance from the optic axis (radial distance in the x-y plane), c is the curvature, k is a conic constant and $A_i$ are aspheric constants. By utilizing the appropriate aspheric constants in designing the base curvature, the desired spherical aberration may be introduced. Different amounts of negative spherical aberration may be introduced across the posterior surface 114. Alternatively, the entire posterior surface 114 may have a particular negative spherical aberration. Thus, the base curvature 130 can be selected to provide the desired level of negative spherical aberration for at least the far focus.

In the embodiment shown in FIG. 2, the diffractive structure 120 introduces a positive spherical aberration into the near focus. Thus, the spherical aberration introduced by the diffractive structure 120 is opposite in sign to that introduced by the base curvature. The spherical aberration is introduced only in the near focus because the nature of diffraction gratings and diffractive optics allow the diffractive structure 120 to affect near performance much more strongly than distant performance.

The diffractive structure 120 is essentially a diffraction grating. The diffractive structure 120 is shown with respect to a dotted line corresponding to a lens on which no diffractive structure is provided. The diffractive structure 120 includes echelettes 122. For simplicity, only two echelettes 122 are labeled. However, another number are present. The size and spacing of the echelettes may vary across the surface of the lens 110. For example, the lens 110 may be divided into zones based on the distance from the optic axis (e.g. along the radius). Different zones may have different step heights for the echelettes 122 and/or different spacings between the echelettes. Thus, the characteristics of the diffractive structure 120 may be controlled by configuring the echelettes 122. The profile of the diffractive structure 120 is given by:

$$z_{diffractive} = P_2 r^2 + P_4 r^4 + P_6 r^6 + \quad (2)$$

where $z_{diffractive}$ is the profile in the z-direction of the diffractive structure 120, r is the distance from the optic axis (radial distance), $P_2$ defines the add power and $P_4$ and $P_6$ are parameters that modify the light distribution. By appropriately configuring the geometry of the echelettes and thus the $z_{diffractive}$, the desired amount of positive spherical aberration may be introduced into the near focus. For example, changing the spacing between the echelettes 122 further from the optic axis (higher radius) may introduce a positive spherical aberration.

The magnitude of the positive spherical aberration provided by the diffractive structure 120 may exceed a negative spherical aberration introduced by the base curvature 120. The net result is that the far focus and near focus may have different spherical aberrations. For example, the far focus may have a negative spherical aberration and the near focus has a positive spherical aberration introduced by the combination of the base curvature 130 and the diffractive structure 120. Thus, the lens 110 may have spherical aberration of opposite signs for the near and far focuses.

The lens 110 may have improved performance while maintaining the benefits of a multifocal lens. Because the lens 110 is a multifocal lens, the ophthalmic device 100 may be used to treat conditions such as presbyopia. Because the diffractive structure 120 and the base curvature 130 provide opposite spherical aberrations in the near and far focuses, the visual disturbances for the lens 110 may be reduced. The effect of the introduction of spherical aberrations having opposite signs may be understood as follows. Multifocal lenses form multiple images of each object. One image is formed for each focus. One of these images will be more focused than the remaining images. For example, for a bifocal lens, two images are formed: one for the near focus and one for the far focus. For a nearby object, a first image formed due to the near focus is in focus. A second image of the nearby object formed due to the far focus has greater defocus/is less focused. This second image is an unwanted artifact. The combination of the diffractive structure 120 and base curvature 130 introduce spherical aberrations that have different signs for different focuses. These spherical aberrations make the image(s) that are less focused less conspicuous. This is accomplished by reducing the contrast and overall visibility of the image(s) having greater defocus. In the example above, the introduction of negative spherical aberration for the far focus results in the image of the near object being more defocused. The second image described above is more defocused, less intense and of more uniform intensity. Similarly, the introduction of positive spherical aberration for the near focus results in the near focus providing a larger, lower intensity, more uniform intensity defocused image for far objects. Thus, the introduction of spherical aberration having opposite signs in the near and far focuses may reduce image artifacts.

Figure 3A:
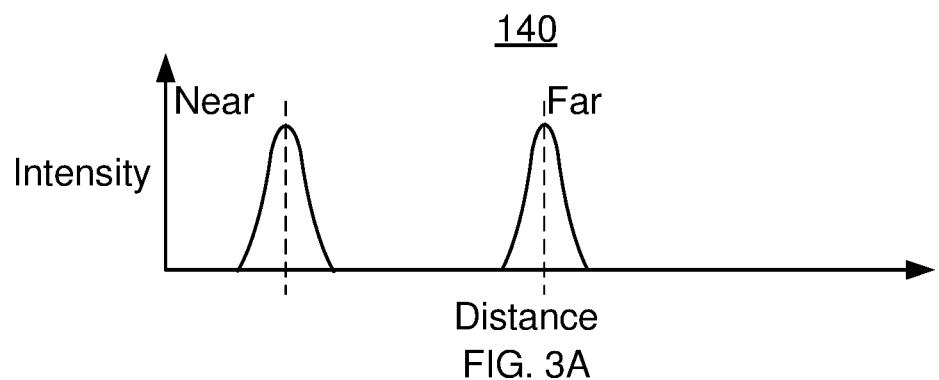
FIGS. 3A-3D depict exemplary embodiments of a the intensity versus distance for lenses made without spherical aberration and with negative spherical aberration in the near focus and positive spherical aberration in the far focus.
Figure 3B:
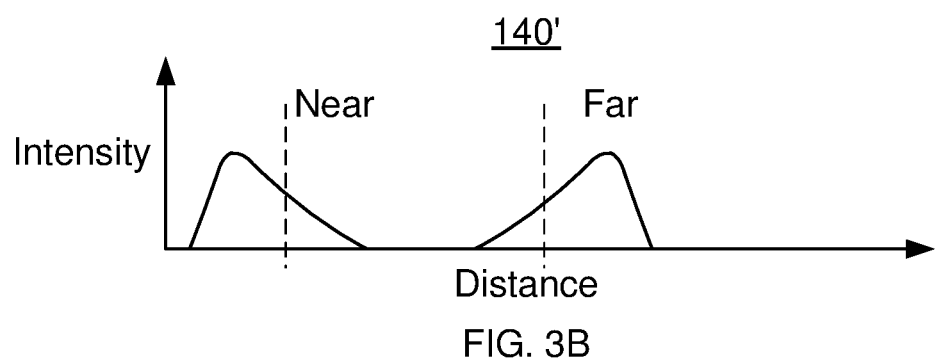
Figure 3C:
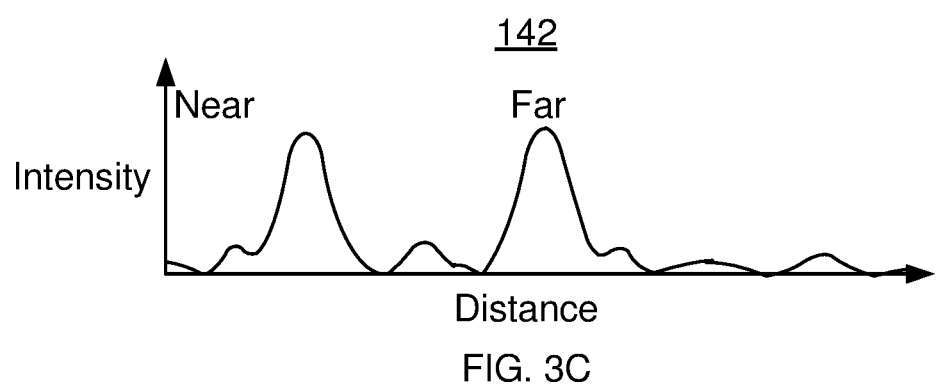
Figure 3D:
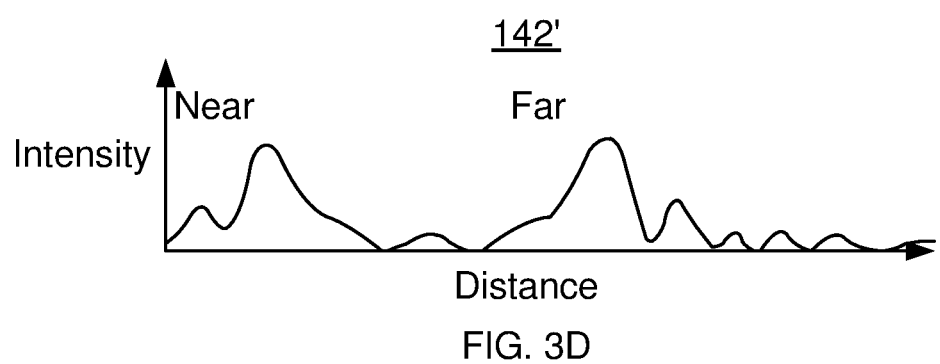

The changes in focus due to the introduction of spherical aberration may also be understood graphically. For example, FIGS. 3A and 3B are schematics illustrating the behavior of two lenses. FIG. 3A is a graph 140 depicting intensity versus distance without spherical aberrations. The near focus and far focus are also indicated in FIG. 3A. As can be seen in FIG. 3A, the intensity peaks in both near focus and the far focus. FIG. 3B is a graph 140' depicting intensity versus distance under the same conditions but for a lens having a positive spherical aberration in the near focus and a negative spherical aberration in the far focus. Thus, the graph 140' corresponds to a lens analogous to the lens 110 depicted in FIGS. 1-2. As can be seen in FIG. 3B, the energy profile has been changed from that shown in FIG. 3A. The peaks in the graph 140' are spread out and asymmetric because of the added spherical aberration. As discussed above, a positive spherical aberration in the near focus results in the corresponding image from a distant object being less focused. Similarly, a negative spherical aberration in the far focus results in the corresponding image of a near object being less focused. As a result, the intensity of a defocused, ghost image may be reduced. Further, the depth of field has been increased. FIGS. 3C and 3D depict analogous graphs 142 and 142' having more realistic characteristics. FIGS. 3C and 3D show the cases without spherical aberration and with positive spherical aberration in the near focus and a negative spherical aberration in the far focus. Thus, the graph 142' thus corresponds to a lens analogous to the lens 110. As can be seen in the by comparing graphs 142 and 142', the energy in each peak in the graph 142' has been asymmetrically spread out. Consequently, visual disturbances such a ghost images may be decreased in intensity while improving depth of field. As a result, performance of the ophthalmic lens 110 may be improved.

Figure 4:
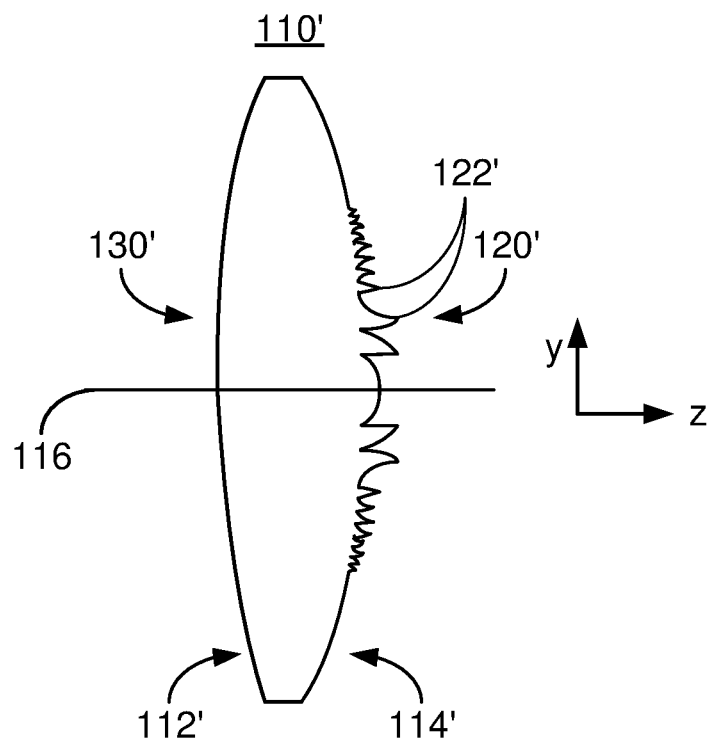
FIG. 4 depicts a side view of another exemplary embodiment of a lens of an ophthalmic device.

FIG. 4 depicts a side view of another exemplary embodiment of a lens 110' of an ophthalmic device. The lens 110' is analogous to the lens 110. Consequently, the lens 110' may be used in an ophthalmic devices such as the device 100. Further, analogous components have similar labels. The lens 110' includes an anterior surface 112', a posterior surface 114', an optic axis 116, base curvature 130' and diffractive structure 120' having echelettes 122' that are analogous to the anterior surface 112, posterior surface 114, optic axis 116, base curvature 130 and diffractive structure 120 having echelettes 122, respectively, of the lens 110.

The diffractive structure 120' resides on the posterior surface 114', while the base curvature 130' resides on the anterior surface 112'. The diffractive structure 120' and base curvature 130' introduce spherical aberrations having opposite signs and, in some embodiments, different magnitudes. Thus, the base curvature 130' may introduce a negative spherical aberration for the at least the far focus. A negative spherical aberration may be provided for the near focus also. The diffractive structure 120' introduces a positive spherical aberration for the near focus. The combination of the diffractive structure 120' and the base curvature 130' may, therefore, provide spherical aberrations having opposite signs in the near and far focus. The intensity profiles for the lens 110' may thus be analogous to those 140' and/or 142' of the lens 110.

The lens 110' may share the benefits of the lens 110. In particular, the lens 110' may have improved performance while maintaining the benefits of a multifocal lens. Because the lens 110' is a multifocal lens, the ophthalmic device 100 may be used to treat conditions such as presbyopia. Because the diffractive structure 120' and the base curvature 130' are employed, the visual disturbances for the lens 110' may be reduced. More specifically, visual disturbances such a ghost images may be decreased in intensity and depth of field improved. As a result, performance of the ophthalmic lens 110' may be enhanced.

Figure 5:
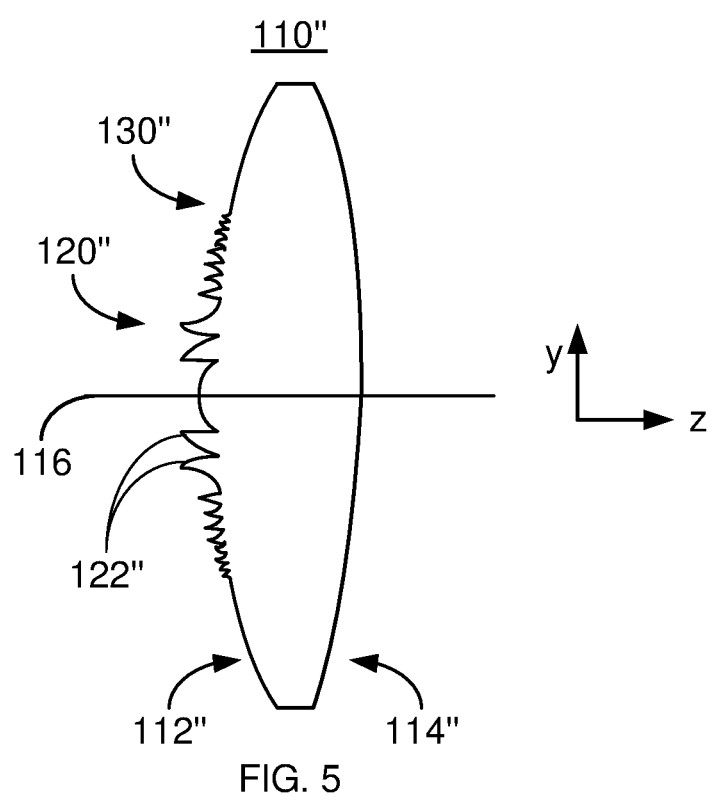
FIG. 5 depicts a side view of another exemplary embodiment of a lens of an ophthalmic device.

FIG. 5 depicts a side view of another exemplary embodiment of a lens 110" of an ophthalmic device. The lens 110" is analogous to the lens(es) 110 and/or 110'. Consequently, the lens 110" may be used in an ophthalmic devices such as the device 100. Further, analogous components have similar labels. The lens 110" includes an anterior surface 112", a posterior surface 114", an optic axis 116, base curvature 130" and diffractive structure 120" having echelettes 122" that are analogous to the anterior surface 112/112', posterior surface 114/114', optic axis 116, base curvature 130/130' and diffractive structure 120/120' having echelettes 122/122', respectively, of the lens(es) 110/110'.

In the lens 110", the diffractive structure 120" and base curvature 130" both reside on the anterior surface 112". This is possible because the profile of the anterior surface 112" is the sum of the profiles of the diffractive structure 120" and the base curvature 130". The diffractive structure 120" and base curvature 130" introduce spherical aberrations having opposite signs and, in some embodiments, different magnitudes. Thus, the base curvature 130" may introduce a negative spherical aberration for the at least the far focus. The diffractive structure 120" introduces a positive spherical aberration for the near focus. The combination of the diffractive structure 120" and the base curvature 130" may provide spherical aberrations having opposite signs in the near and far focus. The intensity profiles for the lens 110" may thus be analogous to those 140' and/or 142' of the lens 110.

The lens 110" may share the benefits of the lens(es) 110 and/or 110'. The lens 110" may have improved performance while maintaining the benefits of a multifocal lens. Because the lens 110" is a multifocal lens, the ophthalmic device 100 may be used to treat conditions such as presbyopia. Because the diffractive structure 120" and the base curvature 130" are employed, the visual disturbances for the lens 110" may be reduced. More specifically, visual disturbances such a ghost images may be decreased in intensity and depth of field improved. As a result, performance of the ophthalmic lens 110" may be enhanced.

Figure 6:
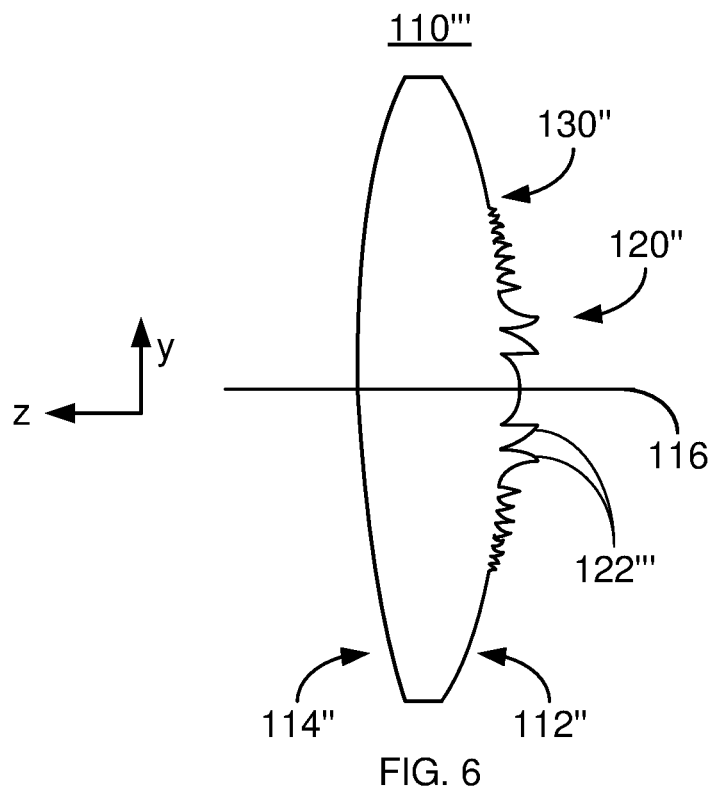
FIG. 6 depicts a side view of another exemplary embodiment of a lens of an ophthalmic device.

FIG. 6 depicts a side view of another exemplary embodiment of a lens 110''' of an ophthalmic device. The lens 110''' is analogous to the lens(es) 110, 110' and/or 110". Consequently, the lens 110''' may be used in an ophthalmic devices such as the device 100. Further, analogous components have similar labels. The lens 110''' includes an anterior surface 112''', a posterior surface 114''', an optic axis 116, base curvature 130''' and diffractive structure 120''' having echelettes 122''' that are analogous to the anterior surface 112/112'/112", posterior surface 114/114'/114", optic axis 116, base curvature 130/130'/130" and diffractive structure 120/120'/120" having echelettes 122/122'/122", respectively, of the lens(es) 110/110'/110".

In the lens 110''', the diffractive structure 120''' and base curvature 130''' both reside on the posterior surface 114'''. The lens 110''' is thus most analogous to the lens 110". The profile of the posterior surface 114''' is the sum of the profiles of the diffractive structure 120''' and the base curvature 130'''. The diffractive structure 120''' and base curvature 130''' introduce spherical aberrations having opposite signs and, in some embodiments, different magnitudes. Thus, the base curvature 130''' may introduce a negative spherical aberration for the at least the far focus. The diffractive structure 120''' introduces a positive spherical aberration for the near focus. The combination of the diffractive structure 120''' and the base curvature 130''' may, therefore, provide spherical aberrations having opposite signs in the near and far focus. The intensity profiles for the lens 110''' may thus be analogous to those 140' and/or 142' of the lens 110.

The lens 110''' may share the benefits of the lens(es) 110, 110' and/or 110". The lens 110''' may have improved performance while maintaining the benefits of a multifocal lens. Because the lens 110''' is a multifocal lens, the ophthalmic device 100 may be used to treat conditions such as presbyopia. Because the diffractive structure 120''' and the base curvature 130''' are employed, the visual disturbances for the lens 110''' may be reduced. More specifically, visual disturbances such a ghost images may be decreased in intensity and depth of field improved. As a result, performance of the ophthalmic lens 110''' may be enhanced.

Figure 7:
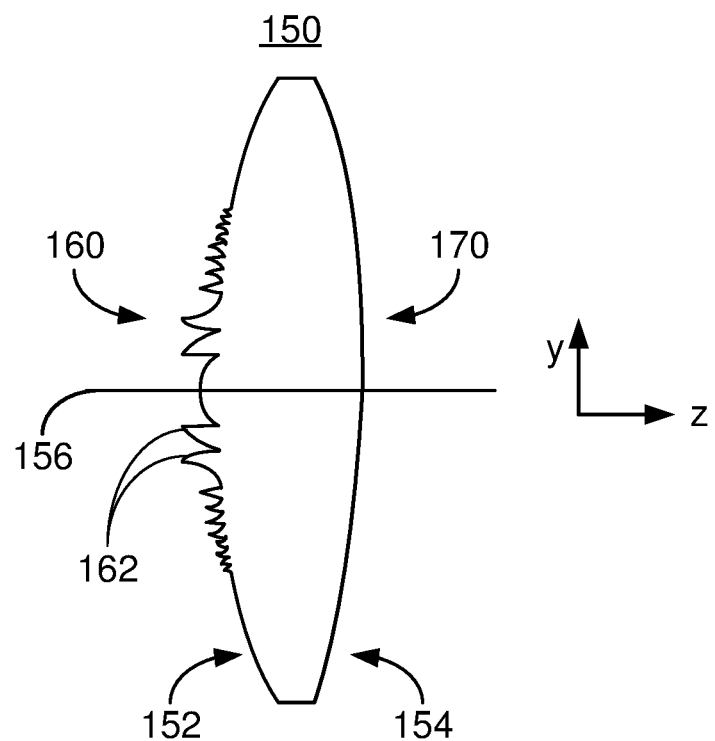
FIG. 7 depicts a side view of another exemplary embodiment of a lens of an ophthalmic device.

FIG. 7 depicts a side view of another exemplary embodiment of a lens 150 of an ophthalmic device. The lens 150 is analogous to the lens(es) 110, 110', 110" and/or 110'''. Consequently, the lens 150 may be used in an ophthalmic devices such as the device 100. Further, analogous components have similar labels. The lens 150 includes an anterior surface 152, a posterior surface 154, an optic axis 156, base curvature 170 and diffractive structure 160 having echelettes 162 that are analogous to the anterior surface 112/112'/112'/112", posterior surface 114/114'/114"/114''', optic axis 116, base curvature 130/130'/130"/130''' and diffractive structure 120/120'/120"/120''' having echelettes 122/122'/122"/122''', respectively, of the lens(es) 110/110'/110"/110'''.

In the lens 150, the diffractive structure 160 resides on the anterior surface 152, while the base curvature 170 resides on the posterior surface 154. Thus, the lens 150 may be considered most analogous to the lens 110. In addition, the lens 150 is a trifocal lens. In other embodiments, the lens 150 may have another number of focuses. For example, the lens 150 might be a quadrafocal lens.

The diffractive structure 160 and base curvature 170 introduce spherical aberrations having opposite signs and, in some embodiments, different magnitudes. Thus, the base curvature 170 may introduce a negative spherical aberration for the at least the far focus. The base curvature 170 may also provide a negative spherical aberration for the near and/or intermediate focuses. The diffractive structure 160 may introduce two spherical aberrations for the intermediate focus and the near focus. For example, the diffractive structure 10 may have a first positive spherical aberration for the near focus and a second positive spherical aberration for the intermediate focus. In some cases, the second spherical aberration has a smaller magnitude than the first spherical aberration. The near and far intensity profiles for the lens 150 may thus be analogous to those 140' and/or 142' of the lens 110. Thus, at least the near and far focus have spherical aberrations that are opposite in sign. The intensity profile for the intermediate focus may be analogous.

Figure 8:
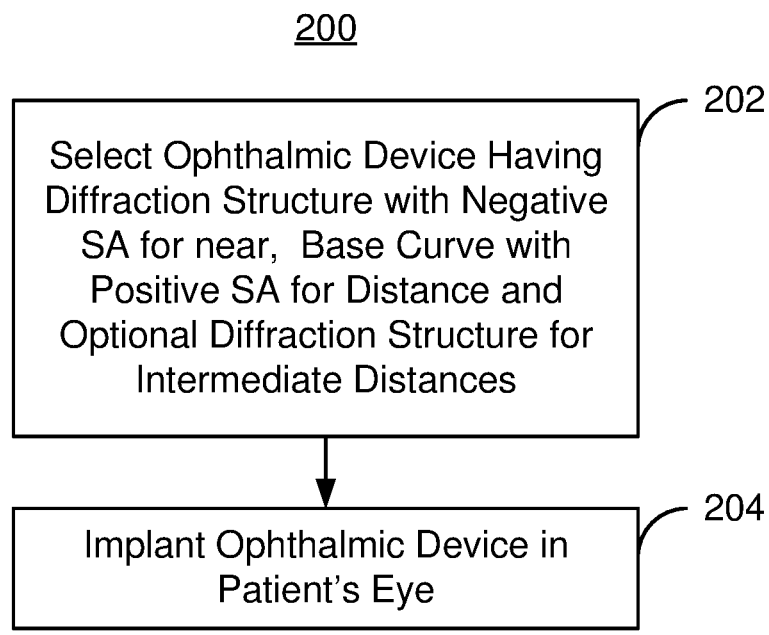
FIG. 8 is flow chart depicting an exemplary embodiment of a method for utilizing an ophthalmic device.

The lens 150 may share the benefits of the lens(es) 110, 110', 110" and/or 110'''. The lens 150 may have improved performance while maintaining the benefits of a multifocal lens. Because the lens 150 is a multifocal lens, the ophthalmic device 100 may be used to treat conditions such as presbyopia. Because the diffractive structure 160 and the base curvature 170 are employed, the visual disturbances for the lens 150 may be reduced. More specifically, visual disturbances such a ghost images may be decreased in intensity and depth of field improved. As a result, performance of the ophthalmic lens 150 may be enhanced FIG. 8 is an exemplary embodiment of a method 200 for treating an ophthalmic condition in a patient. For simplicity, some steps may be omitted, interleaved, and/or combined. The method 200 is also described in the context of using the ophthalmic device 100 and ophthalmic lens 110. However, the method 200 may be used with one or more of ophthalmic lenses 110, 110', 110", 110''' and/or an analogous ophthalmic device.

An ophthalmic device 100 for implantation in an eye of the patient is selected, via step 202. The ophthalmic device 100 includes an ophthalmic lens 110 having a diffractive structure 120 and base curvature 130 that introduce spherical aberrations having opposite sign and, optionally, magnitude. Thus, the ophthalmic device 100 including the ophthalmic lens 110, 110', 110", or 110''' may be selected in step 202.

The ophthalmic device 100 is implanted in the patient's eye, via step 204. Step 204 may include replacing the patient's own lens with the ophthalmic device 100 or augmenting the patient's lens with the ophthalmic device. Treatment of the patient may then be completed. In some embodiments implantation in the patient's other eye of another analogous ophthalmic device may be carried out.

Using the method 200, the ophthalmic lens(s) 110, 110', 1110", 110''' and/or ophthalmic lens may be used. Thus, the benefits of one or more of the ophthalmic lenses 110, 110', 110", and/or 110''' may be achieved.

A method and system for providing an ophthalmic device have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. An ophthalmic lens comprising:
    an anterior surface having an anterior surface base curvature;
    a posterior surface having a posterior surface base curvature, wherein the anterior surface base curvature and the posterior surface base curvature are adapted to provide a base power defining a first focus corresponding to a first focal length and a first spherical aberration corresponding to the first focus; and
    a diffractive structure disposed on one of the anterior surface and the posterior surface, the diffractive structure adapted to:
        split light between the first focus corresponding to the first focal length and a second focus corresponding to a second focal length;
        provide a second spherical aberration corresponding to the second focus, the second spherical aberration having an opposite sign relative to the first spherical aberration; and
        provide a third focus and a third spherical aberration corresponding to the third focus, wherein a magnitude of the third spherical aberration is less than a magnitude of the second spherical aberration.

2. The ophthalmic lens of claim 1, wherein the diffractive structure includes a first diffractive order for the first focus and a second diffractive order for the second focus.

3. The ophthalmic lens of claim 2, wherein the first diffractive order is the 0th order and the second diffractive order is the 1st order.

4. The ophthalmic lens of claim 1, wherein the first spherical aberration is a negative spherical aberration and the second spherical aberration is a positive spherical aberration.

5. The ophthalmic lens of claim 1, wherein the first focus corresponds to distance vision and the second focus corresponds to near vision.

6. The ophthalmic lens of claim 1, wherein the first spherical aberration has a first magnitude and the second spherical aberration has a second magnitude greater than the first magnitude.

7. The ophthalmic lens of claim 1, wherein the diffractive structure is adapted to split light between the first focus corresponding to the first focal length, the second focus corresponding to the second focal length, and a third focus corresponding to an intermediate focal length that is between the first focal length and the second focal length.

8. The ophthalmic lens of claim 1, wherein the ophthalmic lens is one of an intraocular lens and a contact lens.

9. An intraocular lens comprising:
    an anterior surface having an anterior surface base curvature and a posterior surface having a posterior surface base curvature, the anterior surface base curvature and the posterior surface base curvature collectively disposed to provide:
        a base power defining a far focus corresponding to a first focal length; and
        a negative spherical aberration corresponding to the far focus and having a first magnitude; and
    a diffractive structure disposed on one of the anterior surface and the posterior surface, the diffractive structure disposed to:
        distribute light between the far focus corresponding to the first focal length and a near focus corresponding to a second focal length;
        provide a positive spherical aberration corresponding to the near focus and having a second magnitude; and
        provide a spherical aberration corresponding to a third focus, wherein a third magnitude of the spherical aberration is less than the second magnitude of the positive spherical aberration.

10. The intraocular lens of claim 9, wherein the second magnitude of the positive spherical aberration is greater than the first magnitude of the negative spherical aberration.

11. The intraocular lens of claim 9, wherein the diffractive structure is further adapted to distribute light to an intermediate focus between the far focus and the near focus.

12. The intraocular lens of claim 11, wherein the sign of the spherical aberration is positive.

13. An ophthalmic lens, comprising:
an optic having a base curvature adapted to provide a base power defining a first focus and a first spherical aberration corresponding to the first focus; and
a diffractive structure adapted to provide:
   a second focus and a second spherical aberration corresponding to the second focus, the second spherical aberration having an opposite sign relative to the first spherical aberration; and
   a third focus and a third spherical aberration corresponding to the third focus, the third focus corresponding to an intermediate focal length between a first focal length of the first focus and a second focal length of the second focus;
   wherein a magnitude of the third spherical aberration is less than a magnitude of the second spherical aberration.

14. The ophthalmic lens of claim 13, wherein the first focus corresponds to distance vision, and the second focus corresponds to near vision.

15. The ophthalmic lens of claim 13, wherein the first spherical aberration is a negative spherical aberration, the second spherical aberration is a positive spherical aberration, and the third spherical aberration is a positive spherical aberration.

16. The ophthalmic lens of claim 13, wherein the ophthalmic lens is one of an intraocular lens and a contact lens.

* * * * *